United States Patent [19]

Jenkins

[11] 4,277,227
[45] Jul. 7, 1981

[54] APPARATUS FOR CONVERTING A PUMP TO A CONTROLLER

[75] Inventor: Jon A. Jenkins, Rancho Santa Fe, Calif.

[73] Assignee: Imed Corporation, San Diego, Calif.

[21] Appl. No.: 53,981

[22] Filed: Jul. 2, 1979

[51] Int. Cl.³ .................. B04B 21/00; A61M 5/20
[52] U.S. Cl. ........................... 417/63; 128/214 E; 200/83 S; 200/83 Y
[58] Field of Search ............. 417/63, 214, 38, 45; 128/214 E, 214 F, DIG. 12, DIG. 13; 250/551; 200/83 R, 83 J, 83 S, 83 Y

[56] References Cited

U.S. PATENT DOCUMENTS

| 1,568,035 | 12/1925 | Reynolds | 417/214 |
|---|---|---|---|
| 2,435,143 | 1/1948 | Knauth | 200/83 J |
| 3,091,239 | 5/1963 | Moeller | 128/214 F |
| 3,490,342 | 1/1970 | Reis | 200/83 S |
| 3,738,776 | 6/1973 | Debare | 417/38 |
| 3,855,515 | 12/1974 | Hutchins | 417/38 |
| 3,985,133 | 10/1976 | Jenkins | 128/214 F |
| 4,131,393 | 12/1978 | Magnussen | 417/45 |
| 4,142,524 | 3/1979 | Jassawalla | 128/214 F |

*Primary Examiner*—Robert W. Jenkins
*Attorney, Agent, or Firm*—Ellsworth R. Roston; Charles H. Schwartz

[57] ABSTRACT

Apparatus is provided for assuring that fluid is introduced from a pump to a receiver, such as a patient, at a controlled and safe pressure. This arrangement includes conduit means, such as inlet and outlet lines, which extend from the pump to the receiver and which are included in a disposable unit. The disposable unit includes detent means cooperative with detent means in the pump to hold the disposable unit in releasable relationship with the pump.

Resilient means such as diaphragm are disposed in the conduit means in the disposable unit. The resilient means expand or contract in accordance with the pressure of the fluid in the outlet line. Actuatable means such as an actuatable arm is disposed in the disposable unit and is captured in the conduit means and is positioned in abutting relationship with the diaphragm for movement with the diaphragm.

When the pressure of the fluid in the output line reaches a particular value, the actuating arm becomes displaced through a particular distance to operate sensing means external to the disposable unit. The operation of the sensing means causes an output indicator to be energized.

The particular pressure for operating the sensing means is dependent upon the adjustable positioning of control means, such as a knob, external to the disposable unit. The manual adjustment of the knob causes a control member to be adjusted in position. The adjustment in the position of the control member may produce a corresponding adjustment in the force required to actuate the arm, thereby producing an adjustment in the fluid pressure at which the sensing means becomes operative.

40 Claims, 5 Drawing Figures

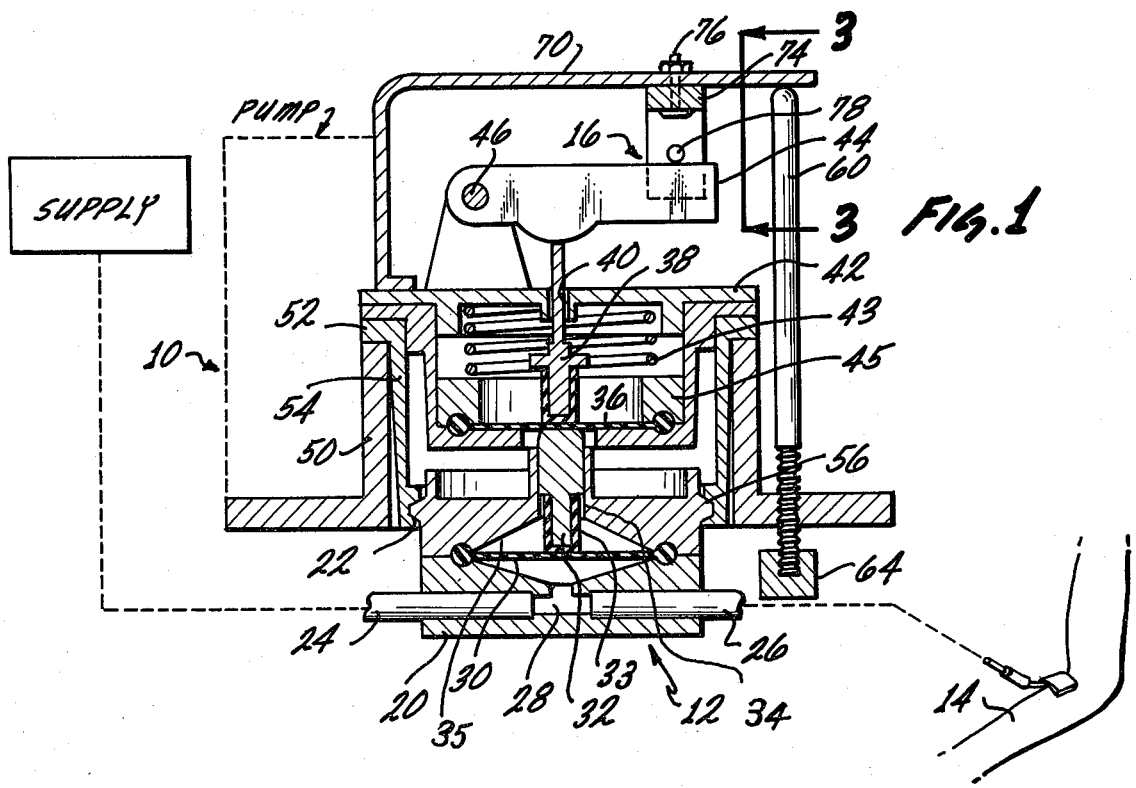

APPARATUS FOR CONVERTING A PUMP TO A CONTROLLER

This invention relates to apparatus for use with a pump for controlling the pressure introduced from the pump to a receiver such as a patient. More particularly, the invention relates to apparatus for controlling the pressure of the fluid introduced from a pump to a receiver such as a patient to assure that the pressure of a fluid introduced to the patient is within selected limits.

Various instrumentalities have been provided in recent years for introducing fluid to a patient. For example, various pumps have been provided for pumping fluid to a patient at a particular rate on a positive basis. For example, U.S. Pat. No. 3,985,133 issued to me, ORRIS H. FLATTEN and OSCAR E. HYMAN as joint inventors and assigned of record to the assignee of record of this application discloses and claims a volumetric pump which introduces a controlled amount of fluid at a pre-selected rate to a patient.

Although pumps are advantageous in that they introduce fluid to a patient on a positive basis, pumps occasionally offer difficulties in that they may introduce the fluid to the patient at pressures greater than the pressures which would ordinarily be considered desirable. This is particularly true when fluids are introduced to infants or the elderly.

Controllers have also been provided for introducing fluid to a patient on a gravitational basis. Such controllers have been advantageous in that they operate at the relatively low pressures which are indicated for infants and the elderly. However, controllers have been disadvantageous until now in that they have not provided for the flow of controlled amounts of fluid at pre-selected rates to a patient by a positive displacement of fluid.

Until now, no one has provided an instrument with the advantages of both a pump and a controller. Specifically, no one has provided a unit which introduces a controlled amount of fluid to a patient at a low and pre-selected pressure and at a pre-selected rate by a positive displacement of such fluid. No one has specifically provided apparatus which is able to operate with any type of pump to provide such advantages. Considerable efforts have been devoted to providing such a unit but such efforts have not been entirely fruitful.

This invention provides a unit with the advantages of both a pump and a controller. The invention provides the advantages of a pump—actually, any kind of pump—by producing a flow of fluid at a controlled rate by a positive displacement of such fluid. The invention provides the further advantages of a controller by producing the flow of fluid at the low pressures which are indicated even for infants and the elderly.

The invention is also advantageous in providing a disposable cassette which is releasably coupled to a pump to convert the operation of the pump into the operation of a controller. The cassette is advantageous in that all of the fluid flows through the disposable cassette. In this way, each individual cassette can be used for a different patient and can then be removed from the pump and can be replaced by a new cassette when a different patient is treated or a different treatment is applied to the same patient.

In one embodiment of the invention, a disposable cassette is provided with a housing having detent means for a releasable engagement with detent means on a pump. The cassette includes conduit means defining inlet and outlet lines and a chamber between the lines. The inlet line receives fluid from the pump and the outlet line passes the fluid to a patient. Resilient means such as a diaphragm are disposed at a particular position in the chamber and are extendable in accordance with the pressure of the fluid in the chamber. An activating arm is captured in the cassette for movement in accordance with the extension of the diaphragm.

The activating arm may produce the operation of a sensor when the actuating arm has moved through a particular distance. The sensor may be included in a unit forming a part of the pump or it may be provided as a separate unit. When the unit forms a part of the pump, the actuating arm in the cassette may extend a resilient diaphragm on the face of the pump in accordance with the movements of the arm. This resilient diaphragm may in turn actuate a flag in accordance with the extension of the diaphragm. When the flag has been moved through a particular distance, it causes the sensor to be energized. The particular pressure necessary to move the flag through the particular distance may be adjusted by manually adjusting a knob. In this way, the adjustment of the knob controls the fluid pressure at which the sensor becomes energized.

In the drawings:

FIG. 1 is a sectional view, partially schematic, of a pump and of one embodiment of apparatus constituting this invention for operating with the pump to control the pressure of fluid from the pump;

FIG. 2 is a sectional view similar to that shown in FIG. 1 but with the apparatus in position for discontinuing the operation of the pump;

FIG. 3 is an enlarged fragmentary elevational view of sensors included in the apparatus of FIGS. 1 and 2;

Figure 4:
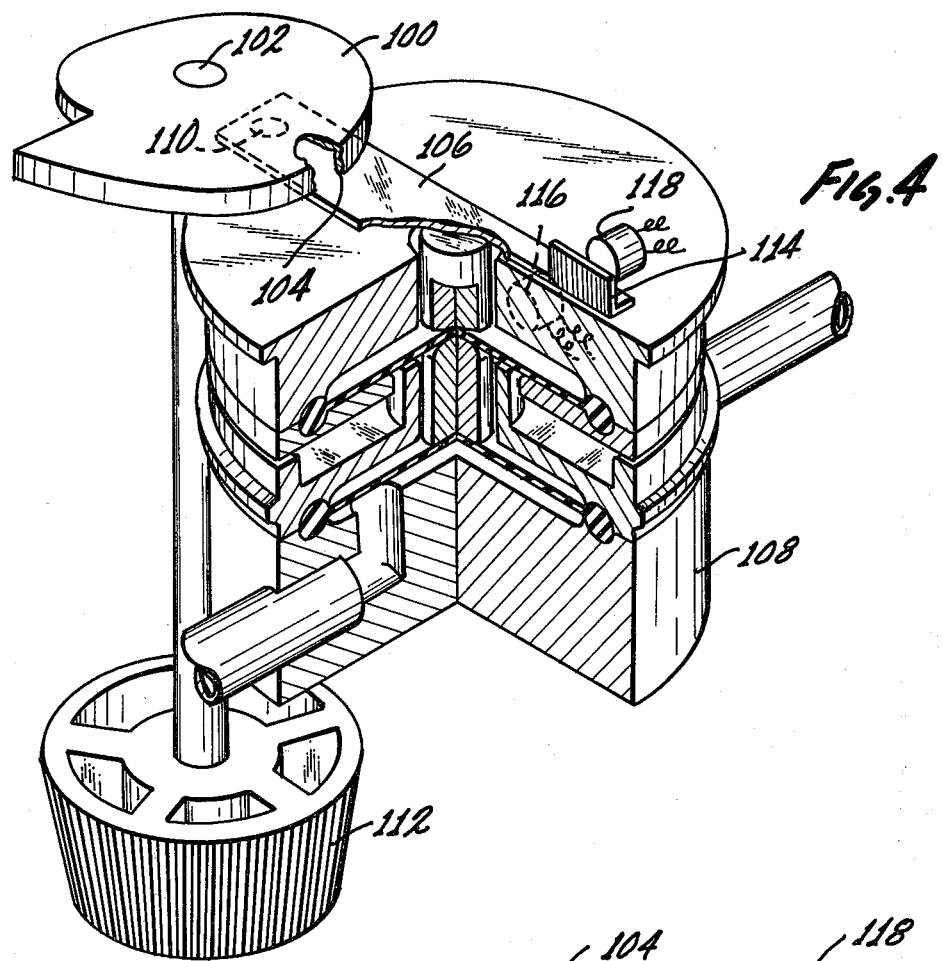
FIG. 4 is a sectional view, partially schematic, of another embodiment of apparatus constituting this operation for operating with a pump to control the pressure of fluid from the pump.

In the embodiment of the invention shown in FIGS. 1 through 3, a pump generally indicated at 10 is provided for pumping fluid at a controlled rate to a patient 14 on a positive basis. The pump 10 may be a volumetric pump such as disclosed and claimed in U.S. Pat. No. 3,985,133. Such a pump is advantageous because it provides a flow of a pre-selected volume of fluid at a precise rate to a patient. However, any other type of pump may also be used.

U.S. Pat. No. 3,985,133 also discloses a disposable cassette for use with the pump. FIG. 1 shows the pump and the disposable cassette in broken lines.

A disposable cassette generally indicated at 12 is coupled to the disposable cassette in the pump 10 to receive fluid from the disposable cassette in the pump and pass the fluid to the receiver such as the patient 14. When the pressure of the fluid in the cassette 12 rises through a particular magnitude dependent upon the setting of a knob 64, sensing apparatus generally indicated at 16 becomes operative to discontinue the operation of the pump. In this way, the pressure of the fluid introduced to the patient is controlled within pre-selected limits.

The cassette 12 is shown in some detail in FIGS. 1 and 2. The cassette 12 includes a housing 20 having detent means such as tongues 22 disposed externally on opposite sides of the housing. The housing 20 is shaped to define conduit means including an inlet line 24, an outlet line 26 and a chamber 28 between the inlet and outlet lines. The chamber 28 communicates with the inlet line 24 and the outlet line 26.

Resilient means such as a diaphragm 30 is stretched across the chamber 28 between opposite sides of the housing 20. An actuatable arm 32 rests on the diaphragm and extends upwardly from the diaphragm through an aperture or opening 34 in the housing. In this way, the arm 32 is captured by the aperture 34. The arm 32 is disposed in cooperative relationship with a reinforcement 33 which extends from the diaphragm. The aperture or opening 34 communicates with a passage 35 which has a dimension converging towards the relatively narrow dimensions of the aperture or opening 34.

When the sensing apparatus 16 is included in the pump, the arm 32 engages resilient means such as a diaphragm 36 on the face of the pump 10. The diaphragm 36 may have a construction similar to that of the diaphragm 30. The diaphragm 36 supports an arm 38 which extends upwardly through a guide aperture 40 in a housing 42 so as to be guided for movement only in a vertical direction. A constrained spring 43 is disposed between the housing 42 and a member 45 seated against the diaphragm 36. A flag 44 is carried at the upper end of the arm 38 and is pivotable at one end on a pin 46 as a fulcrum. The flag 44 carries a light source 48.

A pair of bracket members 50 are supported on the housing 42. Spring members 52 are supported between the housing 42 and the bracket members 50. The spring members 52 are provided with spring arms 54 which include detent means 56 for co-operating with the detent means 22 on the disposable cassette to hold the cassette in releasable relationship.

A lever arm 60 extends through a threaded aperture in one of the bracket members 50. The lever arm 60 receives the knob 64, which is manually rotatable to adjust the vertical positioning of the lever arm 60. At its upper end, the lever arm 60 engages the free end of a spring arm 70, the other end of which is attached to the pump housing 42. A bracket 74 is attached to the housing 42 as by a nut-and-bolt arrangement 76. The bracket 74 carries a photo sensor 78.

When operative, the pump 10 introduces fluid to the inlet line 24. This fluid flows through the chamber 28 and the outlet line 26 to the patient 14. The maximum pressure of this fluid is dependent upon the setting of the knob 64.

It occasionally happens that the outlet line 26 may become occluded. At such times, the fluid in the outlet line 26 rises into the chamber 28. When this back-up of fluid in the outlet line 26 has occurred sufficiently, the fluid in the chamber presses against the diaphragm 30 and forces the diaphragm upwardly. The diaphragm 30 in turn acts upon the arm 32 to force the arm upwardly.

The diaphragm 36 translates the movement of the arm 32 into a corresponding movement of the arm 38. This produces a corresponding pivotal movement of the flag 44 about the pin 46 as a fulcrum. When the flag 44 has moved through a particular distance dependent upon the setting of the knob 64, the light source 48 becomes aligned with the photocell 78. This causes the photocell 78 to become energized and produces a signal for interrupting the operation of the pump 10.

The particular fluid pressure for energizing the photocell 78 can be manually adjusted by rotating the knob 64. This causes the lever arm 60 to be adjusted vertically in position. The adjustment in the vertical position of the lever arm 60 in turn produces adjustments in the pivotal position of the spring arm 70. This in turn produces adjustments in the position at which the light source 48 becomes level with the photocell 78 to energize the photocell.

The apparatus described above has certain important advantages. It provides for a flow of fluid from a pump to a patient at controlled and pre-selected pressures dependent upon the setting of the knob 64. If the pressures of the fluid from the pump should increase above such controlled and pre-selected limits, the apparatus instantaneously senses such increases in the fluid pressure beyond such controlled and safe limits and causes an output signal to be produced for interrupting the operation of the pump.

The apparatus described above also has other important advantages. For example, it provides a cassette which is easily and releasably coupled to the pump. Furthermore, the flow of fluid from the pump to the patient is only through the cassette. In this way, a different cassette can be substituted every time that a different patient is to receive the introduction of fluid or the same patient is to receive a different fluid. By providing such an arrangement, the pump can be easily adapted to provide fluid to a patient at relatively low levels of pressure without requiring that the pump be cleaned or sterilized after each use.

The apparatus constituting this invention also has other advantages. In addition to providing the disposable cassette 12, it provides all of the other elements within the pump housing 42. Furthermore, the diaphragm 36 is disposed at the face of the pump. In this way, the diaphragm 36 helps to seal the pump and also translates the pressure of the fluid on the diaphragm 30 into a corresponding pivotal movement of the flag 44. Although all of the components other than those in the cassette 12 are disposed in the pump housing 42, it will be appreciated that these components can also be disposed in a housing which is separate from the pump.

Figure 5:
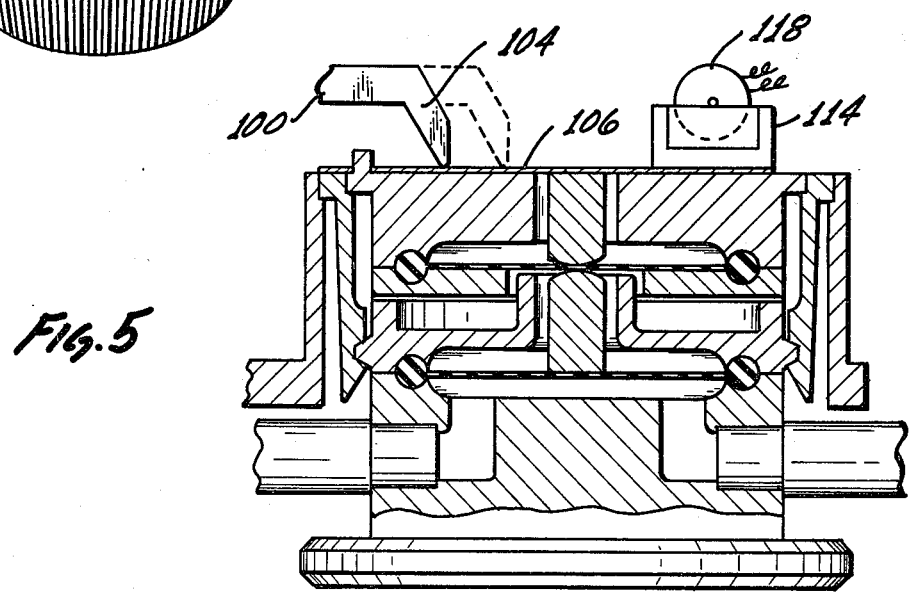
FIG. 5 is a perspective view of the embodiment shown in FIG. 4.

FIGS. 4 and 5 illustrate another embodiment of the invention. In this embodiment, a cam 100 rotatable on a fulcrum 102 is included. The cam includes a finger 104 for contacting a leaf spring 106, the leaf spring being attached at one end to a housing 108 by a screw or protuberance 110. The cam 100 is shaped to move the finger 104 in a direction towards the screw or protruberance 110 in accordance with rotary movements of the cam in a clockwise direction and to move the finger in a direction away from the screw in accordance with rotary movements of the cam in a counter-clockwise direction. The cam 100 is manually rotatable by a knob 112.

The spring 106 carries a flag 114 at the end opposite the screw 110. The flag 114 may interrupt the light from a light source 116 to a sensor 118 when it has moved upwardly through a particular distance. The force required to move the flag 114 upwardly through this particular distance is dependent upon the setting of the cam 100 since this setting controls the length of the torque arm between the finger 104 and the flag. In this way, the setting of the cam 100 controls the fluid pressure at which the light to the sensor 118 becomes interrupted.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:

1. In combination for use with a pump for introducing fluid to a receiver and for controlling the pressure of the fluid introduced by the pump to the receiver, the pump having detent means, an output line for passing the fluid from the pump to the receiver, a resilient diaphragm connected in the output line for constraint in accordance with the pressure of the fluid in the line, means movable with the diaphragm for obtaining the production of an output indication when the pressure of the fluid in the output line has reached a particular level, a housing holding the output line, the diaphragm and the movable means, and detent means on the housing for co-operating with the detent means on the pump for releasably holding the housing in a particular fixed relationship with the pump.

2. The combination set forth in claim 1 wherein the housing is constructed to capture the movable means to provide for a disposition of the movable means on the diaphragm and a movement of the movable means with the diaphragm.

3. The combination set forth in claim 2 wherein the housing defines an output line at one end of the housing and defines an input end at the other end of the housing and defines a chamber between the input and output lines and wherein the diaphragm is disposed in the chamber.

4. The combination set forth in claim 1 wherein means are adjustable to control the force required to move the movable means through each increment of distance in accordance with variations in fluid pressure and wherein means are included for providing the output indication when the movable means has moved through a particular distance.

5. The combination set forth in claim 1 wherein means are adjustable to control the distance through which the movable means is moved to obtain an output indication.

6. The combination set forth in claim 1 wherein the diaphragm is disposed in a particular relationship to the input and output lines in the housing and is stretched across the housing between the input and output lines.

7. In combination for use with a pump for introducing fluid at controlled pressures to a receiver and for providing an output indication when the pressure of the fluid exceeds a particular value, the pump having detent means, conduit means extending from the pump to the receiver to introduce fluid from the pump to the receiver, resilient means included in the conduit means for variable positioning in accordance with variations in the pressure of the fluid in the conduit means, actuatable means operatively coupled to the resilient means for movement with the resilient means to obtain the production of the output indication when the resilient means has reached a particular position, and detent means disposed externally of the conduit means for co-operating with the detent means on the pump to hold the conduit means in a particular fixed relationship to the pump.

8. The combination set forth in claim 7 wherein means are associated with the conduit means for capturing the actuatable means to retain the actuating means for movement with the resilient means.

9. The combination set forth in claim 7 wherein the conduit means define input and output lines and a chamber between the input and output lines and wherein in the conduit means support the resilient means in the chamber at a particular position above the input and output lines.

10. The combination set forth in claim 9 wherein means are associated with the conduit means for capturing the actuatable means to retain the actuatable means for movement with the resilient means and wherein adjustable means are associated with the actuatable means to control the variations in fluid pressure required to produce increments in the movement of the resilient means and the actuatable means.

11. The combination set forth in claim 9 wherein means are associated with the conduit means for capturing the actuatable means to retain the actuating means for movement with the resilient means and wherein adjustable means are associated with the actuatable means to control the variations in the distance of movement of the actuatable means required to obtain the production of the output indication.

12. The combination set forth in claim 7 wherein the resilient means constitutes a diaphragm and the actuatable means constitutes an arm movable with the diaphragm.

13. The combination set forth in claim 7 wherein the resilient means constitutes a diaphragm and the actuatable means constitutes an arm movable with the diaphragm and the adjustable means constitutes a manually movable knob and the variably positioned means constitutes a control lever operatively coupled to the knob for pivotable movement in accordance with the manual adjustments of the knob.

14. The combination for controlling the flow of fluid to a receiver, a pump, conduit means extending from the pump to the receiver to introduce fluid from the pump to the receiver, resilient means included in the conduit means for variable positioning in accordance with variations in the pressure of the fluid in the conduit means, actuatable means included in the conduit means and operatively coupled to the resilient means for movements with the resilient means to obtain the production of the output indication when the resilient means has reached a particular position, sensing means associated with the actuatable means for sensing when the actuatable means has moved through a particular distance, and detent means disposed in cooperative relationship on the pump and the conduit means for retaining the conduit means in a particular fixed, but removable, relationship to the pump.

15. The combination set forth in claim 14 wherein means are associated with the conduit means for capturing the actuatable means to retain the actuating means for movement with the resilient means.

16. The combination set forth in claim 14 wherein the sensing means are included in the pump and wherein the pump also includes resilient means associated with the actuatable means in the conduit means for variable positioning in accordance with the variable positioning of the actuatable means and further includes actuatable means operatively coupled to the resilient means in the pump for movement with such resilient means and wherein the sensing means are included in the pump and are associated with the actuatable means in the pump for sensing when such actuatable means has moved through a particular distance.

17. The combination set forth in claim 14 wherein adjustable means are included for controlling the fluid pressure at which the sensing means becomes operative and means are included in the sensing means for variable positioning in accordance with the adjustment of the adjustable means to control the positioning of the actuatable means at which the sensing means becomes operative.

18. In combination for controlling the flow of fluid to a receiver, a disposable unit including inlet and outlet lines and a chamber between the inlet and outlet lines and a resilient diaphragm disposed in the chamber between the inlet and outlet lines and responsive to the pressure of the fluid in the chamber to become positioned in accordance with such fluid pressure and including detent means, a pump including detent means disposed for cooperation with the detent means on the disposable unit to hold the disposable unit in removable relationship, the pump being constructed to pump fluid to the input line, and means associated with the pump and responsive to the positioning of the resilient diaphragm for interrupting the operation of the pump when the resilient diaphragm has reached a particular position.

19. The combination set forth in claim 18 wherein the means for interrupting the operation of the pump are included in the pump.

20. The combination set forth in claim 19 wherein the means for interrupting the operation of the pump include a resilient diaphragm disposed on the face of the pump and positionable in accordance with the positioning of the diaphragm in the disposable unit and wherein means are disposed in the pump and are responsive to the positioning of the resilient diaphragm in the pump for interrupting the operation of the pump when the resilient diaphragm has reached a particular position.

21. The combination set forth in claim 18 wherein the means for interrupting the operation of the pump are separate from the pump.

22. In combination for controlling the flow of fluid to a receiver, a pump for pumping fluid to the receiver, conduit means for receiving the fluid from the pump and for introducing the fluid to the receiver, first means associated with the conduit means and responsive to variations in the pressure of the fluid in the conduit means for variable positioning in accordance with such variations in fluid pressure, and second means responsive to variations in the positioning of the first means for producing a signal for discontinuing the operation of the pump when the first means has been displaced through a particular distance, the conduit means and the first means being disposed in a cassette and first detent means being provided in the pump and second detent means being provided in the cassette for cooperation with the detent means on the pump to provide a releasable coupling between the cassette and the pump, the conduit means including a housing and inlet and outlet lines, the first means including a chamber between the inlet and outlet lines, and means disposed in the chamber and responsive to the pressure of the fluid in the chamber for variable positioning in accordance with such variations in fluid pressure, the second detent means being disposed on the housing and the first detent means include spring arms on the pump for releasably holding the second detent means.

23. The combination set forth in claim 22 wherein the second means are included in the pump.

24. A method of controlling the pressure of a fluid being pumped from a source to a patient, including the following steps:

providing a pump for pumping the fluid from the source to the patient and operatively coupling the pump between the source and the patient, passing the pumped fluid through a cassette containing a resilient diaphragm constrainable in accordance with the pressure of the fluid passing through the cassette, converting the constraint of the resilient diaphragm to a movement of an output member, providing a member adjustable in positioning and cooperative with the output member to provide an output signal at a position of the output member dependent upon the adjustment in the positioning of the adjustable member, and interrupting the operation of the pump upon the production of the output signal to maintain within particular limits the pressure introduced to the patient, the constrainable diaphragm in the cassette being coupled to a constrainable diaphragm in the pump to produce a constraint of the constrainable diaphragm in the pump in accordance with the constraint of the diaphragm in the cassette and the output member being disposed in the pump and being movable in accordance with the constraint of the diaphragm in the pump and the adjustable member being disposed in the pump.

25. In combination for converting a pump into a controller for controlling within particular limits the pressure of fluid introduced from a source to a patient, a housing having an inlet and an outlet for the flow of fluid and having a chamber in communication with the inlet and the outlet, a resilient diaphragm disposed in the chamber and constrainable in accordance with the pressure of the fluid in the chamber, a pivotable member, a light source, a photocell, means for providing for a variation in the amount of the light passing from the light source to the photocell in accordance with the variations in the positioning of the resilient member, and means responsive to a particular change in the passage of the light from the source to the photocell for indicating that the pressure of the fluid within the housing has exceeded the particular limits.

26. The combination set forth in claim 25, including, detent means on the housing for providing for a removable attachment of the housing to the pump.

27. In combination for converting a pump into a controller for controlling within particular limits the pressure of fluid introduced from a source to a patient, a housing, detent means on the housing for releasable attachment to the pump, an inlet into the housing for receiving the fluid, an outlet from the housing for providing for the transfer of the fluid from the housing, a chamber within the housing in communication within the inlet and the outlet, a diaphragm disposed across the chamber for constraint in accordance with the pressure of the fluid in the chamber, and an arm disposed in communication with the diaphragm for transferring the constraint of the diaphragm as a force into the pump.

28. The combination set forth in claim 27 wherein the diaphragm seals the chamber at one end and wherein the arm extends through the housing for communication with the pump.

29. The combination set forth in claim 27 wherein the housing is provided with an opening at one end in communication with the chamber and wherein the diaphragm is disposed across the opening to seal the chamber from the opening and wherein the diaphragm is constrainable in a direction to extend into the opening in accordance with increases in the pressure of the fluid in the chamber and wherein the arm is extended through the opening to transfer the constraint of the diaphragm into the pump.

30. The combination set forth in claim 29 wherein the housing is shaped to facilitate a manual manipulation of the housing into releasable attachment with the pump and wherein the detent means is disposed on the housing.

31. In combination in a disposable unit for operating in conjunction with a pump to control within particular limits the pressure of fluid introduced from a source to a patient, a housing, detent means on the housing, an inlet for receiving the fluid from the source, an outlet for passing the fluid to the patient, a resilient diaphragm disposed across the chamber to close the chamber and to become constrained in accordance with the pressure of fluid in the chamber, a reinforcement on the diaphragm at an intermediate position on the diaphragm, an opening disposed in the housing in communication with the reinforcement at the end of the housing opposite the chamber, and force-transmitting means disposed in cooperative relationship with the reinforcement and extending through the opening to produce a force in the pump in accordance with the constraint of the diaphragm.

32. The combination set forth in claim 31 wherein the force-transmitting means constitutes an arm disposed in cooperative relationship with the reinforcement and wherein there is a passage in the housing in communication with the opening and the passage is provided with dimensions converging toward the opening and wherein the arm has a tubular portion extending through the passage and the opening to transmit the force on the diaphragm.

33. The combination set forth in claim 32 wherein the reinforcement is hollow and the arm is disposed within the hollow interior of the reinforcement.

34. In combination for controlling the pressure of fluid passing from a source to a patient, a pump for pumping fluid from the source to the patient, a casing supported by the pump, there being a socket in the casing, detent means in the socket, a disposable unit including a housing dimensioned to fit into the socket and including detent means disposed on the housing to cooperate with the detent means in the socket for removably retaining the disposable unit in the socket, there being a chamber in the housing, an inlet disposed in the housing and communicating with the chamber to provide for the introduction of fluid from the source into the chamber, an outlet disposed in the housing and communicating with the chamber to provide for the passage of fluid from the chamber to the patient, a resilient diaphragm disposed in the chamber to close the chamber and constrainable in accordance with the pressure of the fluid in the chamber, and means disposed in the pump and responsive to the constraint of the diaphragm for providing an output indication when the pressure of the fluid in the chamber has reached a particular limit.

35. The combination set forth in claim 34, including, a knob on the face of the pump casing, the knob being adjustable to different positions representing individual limits for the pressure of the fluid in the chamber, and the indicating means including means responsive to the adjustments in the positioning of the knob for providing the output indication when the pressure of the fluid in the chamber has reached the particular limit represented by the adjustments in the positioning of the knob.

36. In combination for controlling within particular limits the pressure of fluid introduced from a source to a patient, a pump for pumping the fluid from the source at a positive pressure, a housing having an inlet and an outlet for the flow of fluid and having a chamber in communication with the inlet and the outlet, a resilient diaphragm disposed in the chamber and constrainable in accordance with the pressure of the fluid in the chamber, means for removably supporting the housing on the pump, means disposed on the pump for adjustably setting the particular limits for the pressure of the fluid flowing through the chamber, and means responsive to the constraint of the diaphragm and the adjustable setting of the particular limits for providing an output indication when the pressure of the fluid in the chamber has reached such particular limits.

37. The combination set forth in claim 36 wherein the indicating means includes a pivotable member and the member is coupled to the diaphragm to receive a force in accordance with the constraint of the diaphragm.

38. In combination for converting a pump into a controller for controlling within particular limits the pressure of fluid introduced from a source to a patient,

- a pump for directing fluid from the source under pressure, the pump including a casing having a receptacle,
- a housing removably disposed within the casing for receiving the fluid directed from the source by the pump and for directing the fluid to the patient,
- resilient means included within the housing for constraint in accordance with the pressure of the fluid in the housing.
- a knob extending externally from the pump casing and adjustable in position from a position external to the pump casing to control within particular limits the pressure of the fluid within the housing, and
- means operatively coupled to the resilient means and the knob for providing an output indication when the resilient means have received a particular constraint dependent upon the setting of the adjustable knob.

39. The combination set forth in claim 38, including, resilient detent means in the casing for removably holding the housing, and
detent means on the housing for cooperation with the resilient detent means in the casing to provide a removable retention of the housing by the casing.

40. The combination set forth in claim 39, there being a socket in the casing for receiving the housing, the resilient detent means being disposed in the socket.

* * * * *